(12) United States Patent
Lee et al.

(10) Patent No.: US 6,421,554 B1
(45) Date of Patent: Jul. 16, 2002

(54) METHOD AND DEVICE FOR DETECTING FAULT OF LEAD IN ELECTROCARDIOGRAM SYSTEM

(75) Inventors: Sang-min Lee; Jong-youn Lee; In-young Kim, all of Seoul (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 09/475,157

(22) Filed: Dec. 30, 1999

(30) Foreign Application Priority Data

Dec. 31, 1998 (KR) .............................. 98-63151

(51) Int. Cl.[7] ............................................ A61B 5/0702
(52) U.S. Cl. ....................................................... 600/509
(58) Field of Search ................................. 600/509, 523

(56) References Cited

U.S. PATENT DOCUMENTS

| | | |
|---|---|---|
| 3,602,215 A | 8/1971 | Parnett |
| 3,859,988 A | 1/1975 | Lencioni, Jr. |
| 3,978,856 A | 9/1976 | Michel |
| 4,124,894 A | 11/1978 | Vick et al. |
| 4,527,567 A | 7/1985 | Fischler et al. |
| 4,658,831 A | 4/1987 | Reinhard et al. |
| 5,029,590 A | 7/1991 | Allain et al. |
| 5,231,990 A | 8/1993 | Gauglitz |
| 5,333,617 A | 8/1994 | Hafner |
| 5,564,429 A | 10/1996 | Bornn et al. |
| 5,649,969 A | 7/1997 | Abrahamson et al. |
| 5,704,351 A | 1/1998 | Mortara et al. |

FOREIGN PATENT DOCUMENTS

| | | |
|---|---|---|
| EP | 0712605 | 5/1996 |
| WO | 83/04369 | 12/1983 |

OTHER PUBLICATIONS

Arthur, et al. "Interactive Acquistion of Diagnostic Electrocarbiograms" pp. 307–311.

Primary Examiner—Scott M. Getzow
(74) Attorney, Agent, or Firm—Lee & Sterba, P.C.

(57) ABSTRACT

A method and device for detecting a lead fault by analyzing a electrocardiogram signal from a telemetric or portable electrocardiogram system using software. In the device for detecting a lead fault, the electrocardiogram signal can be analyzed using software by a microcontroller without an extra microcontroller, so that the size of a telemetric or portable electrocardiogram system can be reduced while also reducing power consumption.

26 Claims, 3 Drawing Sheets

METHOD AND DEVICE FOR DETECTING FAULT OF LEAD IN ELECTROCARDIOGRAM SYSTEM

BACKGROUND OF THE INVENTION

1. Field of the Invention

The present invention generally relates to a method and device for detecting a lead fault of a telemetric or portable electrocardiogram system and, more particularly, to a method and device for detecting a lead fault of a telemetric or portable electrocardiogram system using software by analyzing the input electrocardiogram signal.

2. Description of the Related Art

An electrocardiogram (ECG or EKG) system collects physiological information by attaching lead markers to the body of a subject and analyze and processing the collected information. An ECG signal collector (referred to as a "lead marker") includes an electrode that directly contacts the skin of the subject and a lead wire for connecting the lead marker to the main body of a measurement apparatus. If a lead marker which is attached to the body of a subject for continuous observation is separated from the body, an alarm is produced so that the lead marker can be reattached.

U.S. Pat. No. 3,859,988 discloses a device for detecting a lead fault in a telemetric biomedical system. In this device, a lead marker fault is detected by repeatedly applying a low current signal having a specific waveform and frequency to the lead markers. A specific applied signal is output if at least one lead marker is detached, to indicate fault of the lead marker. Accordingly, the lead fault detection device additionally requires a generator for generating a signal having a specific waveform and a counter for repeatedly transmitting the signal.

Another device for detecting fault of a lead in a telemetric biomedical system is disclosed in U.S. Pat. No. 4,658,831. This device is for detecting lead faults in an ECG. An ECG signal and a pulse signal applied to each lead marker are modulated together by frequency modulation and transmitted wirelessly. The two transmission signals are divided in a receiver and the divided pulse signal is detected in an additional circuit to detect a fault of a lead. This device also requires an additional device such as a pulse signal generator.

Other devices for detecting a lead fault are disclosed in U.S. Pat. Nos. 5,649,969 and 3,602,215. However, these devices also require an additional lead fault detector 11 as show in FIG. 1. The size of a telemetric biomedical system adopting the techniques disclosed in these patents necessitates increases in power consumption. Therefore, they cannot be applied to a small and portable telemetric biomedical system.

SUMMARY OF THE INVENTION

It is a feature of the present invention to provide a method and apparatus for detecting a lead fault in a small and portable ECG system. According to the present invention, a method for detecting a lead fault in an ECG system comprises the steps of: (a) collecting ECG signals from a sensor; (b) removing noise and amplifying the ECG signals; (c) converting signals from step (b) into digital signals; (d) processing the digital signals to analyze the ECG signals; (e) determining whether the ECG signals change using the digital signals; and (f) indicating separation of the ECG signal source from the sensor if the ECG signals do not change in step (e).

In accordance with another aspect of the present invention there is provided a method for detecting a lead fault in an ECG system having an ECG signal collector attached to the body of a subject for collecting ECG signals; a filtering and amplifying portion for removing a noise component from the ECG signals and amplifying the signals; an analog-to-digital converter for converting the ECG signals into digital signals; a controller for processing the digital signals from the analog-to-digital converter to analyze the ECG signals, and a lead fault information display for displaying whether the ECG signal collector is separated from the subject, the method comprising the steps of: (a) determining whether the ECG signals change using the digital signals from the analog-to-digital converter; and (b) if the ECG digital signals do not change in step (a), providing an indication that there is separation of the ECG signal collector using the lead fault information display. Step (a) may further comprise the steps of: determining whether ECG signals are present using the signals from the analog-to-digital converter; if the ECG signals are not present, providing an indication that there is separation of the ECG signal collector via the display; and if the ECG signals are present, comparing the signals from the analog-to-digital converter to digital signals which have the periodicity of ECG signals and are previously stored in a controller; and if the periodicity of the signals from the analog-to-digital converter is different from that of the digital signals previously stored in the controller, providing an indication there is separation of the ECG signal collector. The digital signals which have the periodicity of ECG signals and are previously stored in the controller are expressed as the number of peak values in ECG signals for a predetermined period, and a comparing step is performed by counting the number of peaks or valleys in the signals from an analog-to-digital converter, corresponding to the peak or valley values of the ECG signals, for the predetermined period. A step of comparing the count value to the previously stored number of peak or valley values of the ECG signals is then performed. Also, the digital signals which have the periodicity of ECG signals and are previously stored in the controller may be expressed as the frequency range of ECG signals, and a comparing step may also be performed by measuring the frequency range of the ECG signals from the analog-to-digital converter and comparing the measured frequency range of the ECG signals to that of the digital signals stored in a controller.

In accordance with another aspect of the present invention, there is provided a device for detecting a lead fault in an ECG system comprising: an ECG signal collector for collecting ECG signals, a filtering and amplifying portion for removing noise components and amplifying the ECG signals from the ECG signal collector, an analog-to-digital converter for converting signals from the filtering and amplifying portion into digital signals, a controller for processing the digital signals to analyze the ECG signals, and a comparator for detecting changes in the digital signals corresponding to changes in the ECG signals.

In accordance with yet another aspect of the invention there is provided a device for detecting a lead fault in an ECG system, including an ECG signal collector attachable to the body of a subject for collecting ECG signals; a filtering and amplifying portion for removing noise components from the ECG signals and amplifying the signals, an analog-to-digital converter for converting the ECG signals into digital signals; a controller for processing the digital signals from the analog-to-digital converter to analyze the ECG signals, and a lead fault information display for displaying whether the ECG signal collector is separated from the subject. The device comprising: a controller for determining whether the ECG signals change using the signals from the analog-to-digital signals; and a command portion for providing a command to the lead fault information display to display an alert that indicates separation of the ECG signal collector from the body of the subject, if the controller determines that the ECG signals have changed. The controller determines whether the ECG signals are present using signals from an analog-to-digital converter, and if it is determined that the ECG signals are present, the controller compares the signals from the analog-to-digital converter with digital signals which have been previously stored in a controller and which have the periodicity of ECG signals.

In accordance with yet another aspect of the invention, digital signals which have the periodicity of ECG signals and are previously stored in a controller are expressed as the number of peak or valley values in ECG signals for a predetermined period of time, and a controller counts the number of peaks or valleys in the signals from an analog-to-digital converter corresponding to the peak values of the ECG signals for the predetermined period of time and compares the count value to the previously stored number of peak or valley values of the ECG signals. Additionally, the digital signals which have the periodicity of ECG signals and are previously stored in the controller are expressed as a frequency range of ECG signals, and the controller measures the frequency range of the ECG signals from the analog-to-digital converter and compares the measured frequency range of the ECG signals to that of the digital signals stored in the controller.

In accordance with still another aspect of the present invention, there is provided a device for detecting a lead fault in an ECG system comprising: ECG signal collecting means for collecting ECG signals, filtering and amplifying means for removing noise components and amplifying the ECG signals from the ECG signal collecting means, converting means for converting signals from the filtering and amplifying means into digital signals, processing means for processing the digital signals to analyze the ECG signals, and detecting means for detecting changes in the digital signals corresponding to changes in the ECG signals.

Also, to increase lead fault detection reliability, the input signals can be filtered by using a filter located before the leading end of the microcontroller, or by using software programmed in the microcontroller, prior to the detection of a lead fault.

BRIEF DESCRIPTION OF THE DRAWINGS

The above features and advantages of the present invention will become more apparent by describing in detail preferred embodiments thereof with reference to the attached drawings in which.

DESCRIPTION OF THE PREFERRED EMBODIMENTS

Applicants' Korean application No. 98-6315 filed Dec. 31, 1998, is incorporated herein by reference as if fully set forth herein.

Use of "signal" in the singular also includes the plural form "signals" unless otherwise clear from the usage and context that the singular form is being specified.

In the following embodiments, a device for detecting a lead fault according to the present invention is applied to an electrocardiogram (ECG or EKG). However, the lead fault detection device can be applied to many different telemetric or portable biomedical systems which record physiological signals that have periodicity, e.g., electroencephalograph (EEG).

Figure 1:
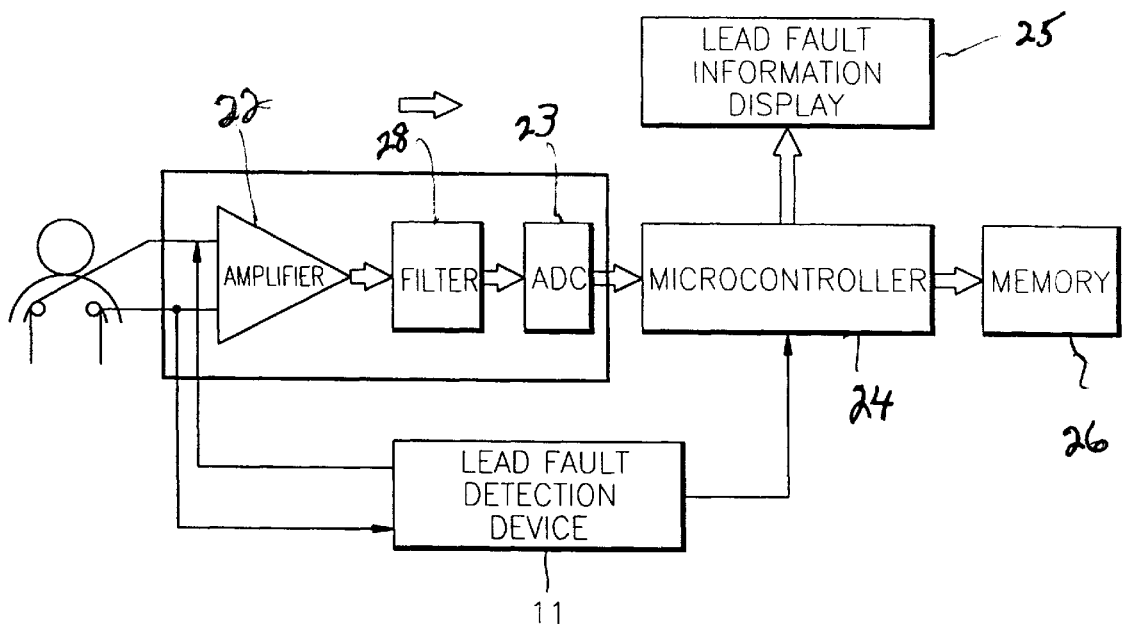
FIG. 1 is a block diagram of a conventional device for detecting a lead fault in an ECG system.
Figure 2:
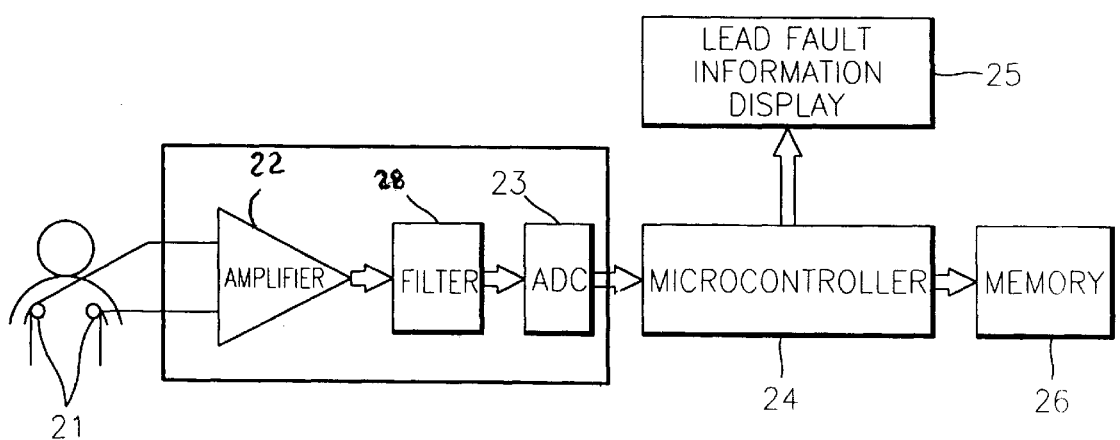
FIG. 2 is a block diagram of a device for detecting a lead fault in an ECG system according to the present invention.

FIG. 2 shows an exemplary device for detecting a lead fault according to the present invention (e.g., an ECG). An ECG signal of a subject is collected by electrodes, for example, lead markers 21 (generally referred to as collectors), attached to the body of a subject and is amplified by an amplifier 22. Noise is removed from the amplified analog signal by a filter 28. The signal is subsequently converted into a digital signal by an analog-to-digital converter (ADC) 23, and is sent to a microcontroller 24. In the microcontroller 24, the ECG signal is processed and a determination is made as to whether the lead marker is separated from the body. If the microcontroller 24 determines that the lead marker is detached, that information is displayed on a lead fault information display 25 for the subject or an operator to see. When the ECG signal is normal, with the lead marker being attached to the body of the subject, the signal is processed by the microcontroller 24 and is stored in the microcontroller memory or an external memory 26. For higher reliability in the detection of a lead fault, a filter 28 may be installed before the microcontroller 24 or an input signal may be filtered using software in the microcontroller prior to the lead detection. The filter 28 removes noise from the signal before supplying it to the microcontroller.

The microcontroller 24 functions as a comparator and as a command unit, however, the comparator and command unit may be separate devices. The comparator determines whether an ECG signal changes. The command unit controls the lead fault information display 25 by providing a command to the lead fault information display 25 to display an alert signal that indicates a lead marker fault when a lead fault is detected in the signal from the ADC 23. The comparator determines whether an ECG signal is input or not by comparing the signal from the ADC 23 to stored signal characteristics. When an ECG signal is input, the comparator compares the signal from the ADC 23 to a digital signal which has a periodicity such as ECG signals and is previously stored in the microcontroller 24. The digital signal having a periodicity of ECG signals may be expressed as the number of peak or valley values of the ECG signal for a predetermined period. That is, the comparator compares the number of peak or valley values of the signal from the ADC 23, which repeat for a predetermined period, to that previously stored in the ADC 23. Alternatively, a digital signal indicating the frequency range of ECG signals can be pre-stored in the microcontroller 24, instead of the periodic characteristics of the ECG digital signal. In this way, the comparator measures the frequency range of the ECG signal from the ADC 23 and compares the measured frequency range to the previously stored digital signal indicating the frequency of the ECG signal.

Figure 3:
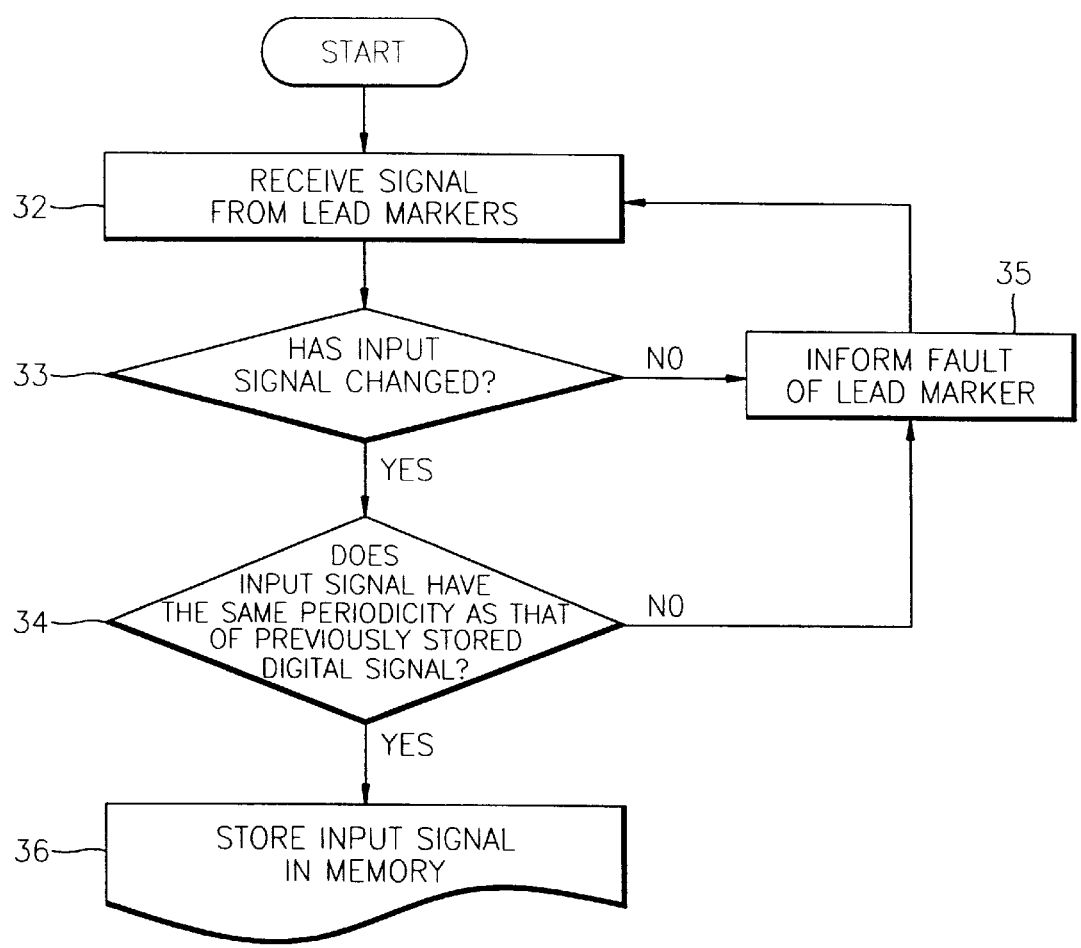
FIG. 3 is a flowchart illustrating a method for detecting a lead fault for the detection device of FIG. 2.
Figure 4:
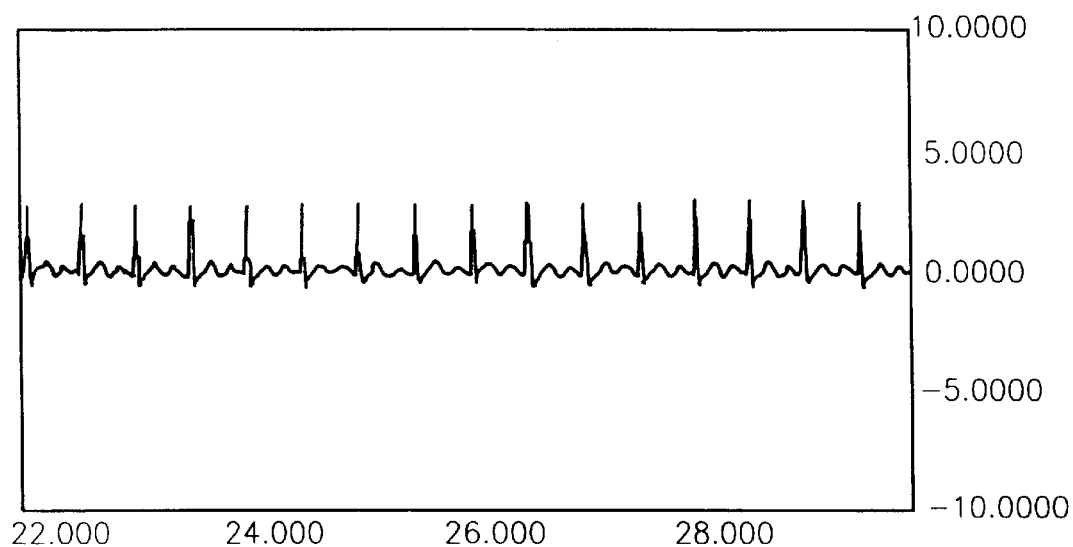
FIG. 4 shows waveforms of a typical electrocardiogram signal.
Figure 5:
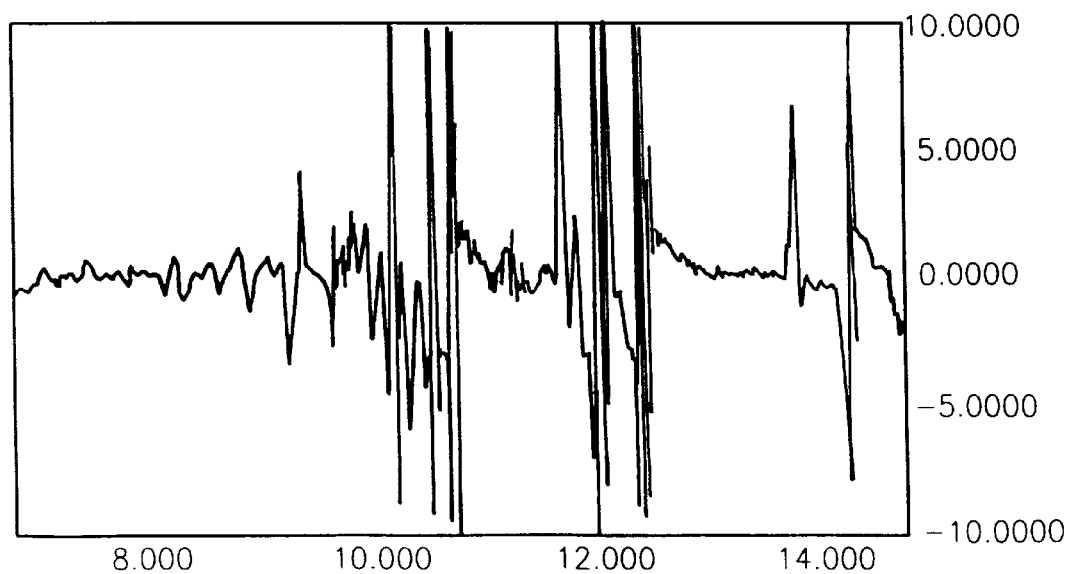
FIG. 5 shows waveforms of an input signal when a lead marker is detached or not properly attached.

FIG. 3 is a flowchart illustrating the detection of a lead fault for the microcontroller 24. When an ECG signal is input from the ADC 23 (step 32), the microcontroller 24 determines whether an input signal changes (step 33). If ECG signals as shown in FIG. 4 or noise signals as shown in FIG. 5 indicating unattached or improperly attached lead markers are input, a determination that the input signal has changed is made, and the process moves to step 34. However, when there is no input signal due to separation of a lead marker from the body of a subject, or an input signal remains constant, the microcontroller 24 sends a warning to the lead fault information display 25. In the step 34, the periodicity of the input signal is compared to that of a previously stored ECG signal. In general, the input signal may change even when the lead marker is separated from the subject. That is, this is the case where electrical noises are input via the lead marker or movement of the subject causes electrical noise. However, electrical noise or movement noises may not have periodicity. Even if electrical noise or movement noise have periodicity, the periodicity is not as long as that of ECG signals, nor do they have the same periodicity as the ECG signals. Thus, when it is determined in step 33 that the input signal has changed, it is only when the input signal is determined to have the same periodicity as that of the pre-stored ECG signals in step 34, that the input signal is stored in a memory (step 36). Otherwise, when the periodicity of the input signal is different from that of the pre-stored ECG signals, the microcontroller 24 sends a warning signal to the lead fault information display 25 to display information about the lead fault.

As described above, the periodicity of the input signal may be determined in step 34 by pre-setting the frequency range of ECG signals and comparing the same to the frequency of the input signal. Alternatively, the periodicity of the input signal may be determined by comparing the number of peak or valley values of the input signal for a predetermined period to the previously stored number of peak or valley values of the ECG signals.

In order to increase the reliability in detection of lead faults, the entire process can be repeated two or more times.

As described above, in the device for detecting fault of a lead in an ECG system according to the present invention, the detection of a lead fault is achieved by analyzing an input physiological signal in a microprocessor, without an additional circuit for detecting lead fault. Thus, the size of the lead fault detection device can be decreased, and power consumption can also be decreased. Also, real-time alarms for detected lead faults are possible, so that a subject or operator can quickly respond.

Thus, a method and apparatus for lead fault detection in an ECG system has been described according to the present invention. While the invention is susceptible to various modifications and alternative forms, specific embodiments have been shown by way of example in the drawings and described in detail herein. However, it should be understood that the invention is not limited to the particular forms disclosed. Rather, the invention covers all modifications, equivalents, and alternatives falling within the spirit and scope of the invention as defined in the appended claims.

What is claimed is:

1. A method for detecting a lead fault in an ECG system, comprising the steps of:
    (a) collecting an ECG signal from a sensor;
    (b) filtering and amplifying the ECG signal;
    (c) converting the signal from step (b) into a digital signal;
    (d) processing the digital signal to analyze the ECG signal;
    (e) determining whether the ECG signal changes using the digital signal; and
    (f) indicating separation of the ECG signal from the sensor if the ECG signal does not change in step (e).

2. The method of claim 1, further comprising the step of displaying the indication of step (f) on a lead fault information display.

3. The method of claim 2, wherein step (e) is performed by determining whether the digital signal has the same periodic characteristics as a previously stored digital signal.

4. The method of claim 3, wherein step (e) is performed by counting the periodic characteristic peaks of the digital signal for a predetermined period corresponding to maximum values of the ECG signal, and comparing the count value to a previously stored number of peak values of the digital signal corresponding to previous maximum values of the ECG signal.

5. The method of claim 3, wherein step (e) is performed by counting the periodic characteristic valleys in the digital signal for a predetermined period corresponding to minimum values of the ECG signal, and comparing the count value to a previously stored number of valley values of the digital signal corresponding to previous minimum values of the ECG signal.

6. The method of claim 3, wherein step (e) is performed by measuring the characteristic frequency range of the digital signal and comparing the measured frequency range to that of a previously stored frequency range corresponding to a previous digital signal.

7. The method of claim 2, wherein step (e) further comprises the steps of:
    (e1) determining whether the ECG signal is input using the digital signal;
    (e2) comparing the digital signal to a previously stored digital signal if the ECG signal is input; and
    (e3) providing an indication of sensor separation via the lead fault information display if the periodicity of the digital signal is different from the previously stored digital signal.

8. The method of claim 7, wherein step (e2) is performed by counting the number of peaks in the digital signal for a predetermined period corresponding to the peak values of the ECG signal, and comparing the count value to a previously stored number of peak values corresponding to a previous ECG signal.

9. The method of claim 7, wherein step (e2) is performed by counting the number of valleys in the digital signal for a predetermined period corresponding to the valley values of the ECG signal, and comparing the count value to a previously stored number of valley values corresponding to a previous ECG signal.

10. The method of claim 7, wherein step (e3) is performed by measuring the frequency range of the digital signal and comparing the measured frequency range to a stored frequency range corresponding to a previous ECG signal.

11. The method of claim 2, wherein steps (e) and (f) are repeated two or more times.

12. A device for detecting a lead fault in a electrocardiogram system, comprising:
    an ECG signal collector for collecting a physiological signal;
    a filtering and amplifying portion for removing a noise component and amplifying the ECG signal from the physiological signal collector;
    an analog-to-digital converter for converting a signal from the filtering and amplifying portion into a digital signal; and
    a controller for processing the digital signal to analyze the ECG signal and for detecting changes in the digital signal corresponding to changes in the ECG signal.

13. The device of claim 12, further comprising:
a lead fault information display responsive to the controller for displaying whether the ECG signal collector is separated from a subject.

14. The device of claim 13, wherein the controller provides a command to the lead fault information display to display an alert indicating separation of the ECG signal collector from the subject, if the controller determines that the digital signal corresponding to the ECG signal has changed.

15. The device of claim 14, wherein the controller responsive to the ECG signal determines whether the ECG signal is inputed, and if it is determined that the ECG signal is input, the controller compares characteristics of the digital signal to those of a previously stored digital signal.

16. The device of claim 15, wherein the characteristics of the previously stored digital signal is expressed as a number of peak values in the ECG signal for a predetermined period, the controller counts the number of peaks in the digital signal for the predetermined period corresponding to the peak values of the ECG signal, and compares the count value to the previously stored signal expressed as the number of peak values in the ECG signal.

17. The device of claim 15, wherein the characteristics of the previously stored digital signal is expressed as the number of valley values in the ECG signal for a predetermined period, the controller counts the number of valleys in the digital signal for the predetermined period corresponding to the valley values of the ECG signal, and compares the count value to the previously stored signal expressed as the number of valley values of the ECG signal.

18. The device of claim 15, wherein the characteristics of the previously stored digital signal is expressed as the frequency range of the ECG signal for a predetermined period corresponding to the frequency range of the ECG signal, the controller compares the frequency range to the previously stored signal expressed as the frequency range of the ECG signal.

19. A device for detecting a lead fault in a ECG system, comprising:
ECG signal collecting means for collecting a ECG signal;
filtering and amplifying means for removing a noise component and amplifying the ECG signal from the ECG signal collecting means;
converting means for converting a signal from the filtering and amplifying means into a digital signal; and
processing means for processing the digital signal to analyze the ECG signal and for detecting changes in the digital signal corresponding to changes in the ECG signal.

20. The device of claim 19, further comprising:
display means responsive to the processing means for displaying whether the ECG signal collecting means is separated from a subject.

21. The device of claim 20, wherein the processing means provides a command to the display means to display an alert indicating separation of the ECG signal collecting means from the subject, if the processing means determine that the digital signal corresponding to the ECG signal has changed.

22. The device of claim 19, wherein the processing means determines whether the ECG signal is input, and if it is determined that the ECG signal is input, the processing means compares the digital signal to a previously stored digital signal.

23. The device of claim 19, wherein the processing means determines whether the ECG signal is input, and if it is determined that the ECG signal is input, the processing means compares a characteristic of the digital signal to a previously stored characteristic of the digital signal.

24. The device of claim 23, wherein the previously stored characteristic is expressed as the number of peak values in the ECG signal for a predetermined period, and the processing means counts the number of peaks in the digital signal for the predetermined period corresponding to the peak values of the ECG signal for the predetermined period, and compares the count value to the previously stored characteristic expressed as the number of peak values in the ECG signal.

25. The device of claim 23, wherein the previously stored characteristic is expressed as the number of valley values in the ECG signal for a predetermined period, and the processing means counts the number of valleys in the digital signal for the predetermined period corresponding to the valley values of the ECG signal for the predetermined period, and compares the count value to the previously stored characteristic expressed as the number of valley values of the ECG signal.

26. The device of claim 23, wherein the previously stored characteristic is expressed as the frequency range of the ECG signal for a predetermined period corresponding to the frequency range of the ECG signal for the predetermined period, and the processing means compares the frequency range to the previously stored characteristic expressed as the frequency range of the ECG signal.

\* \* \* \* \*